US012582347B2

(12) United States Patent
Naviwala et al.

(10) Patent No.: US 12,582,347 B2
(45) Date of Patent: Mar. 24, 2026

(54) APPARATUS, METHODS, AND SYSTEMS FOR MEASURING CERVICAL DILATION USING STRUCTURED LIGHT

(71) Applicant: Frotek LLC, Miramar, FL (US)

(72) Inventors: Farhan Naviwala, Miramar, FL (US); Rafael Carreno, Miami, FL (US); Spencer Duke, Parkland, FL (US)

(73) Assignees: Farhan Naviwala, Miramar, FL (US); Spencer Duke, Parkland, FL (US); Rafael Carreno, Miami, FL (US)

( * ) Notice: Subject to any disclaimer, the term of this patent is extended or adjusted under 35 U.S.C. 154(b) by 731 days.

(21) Appl. No.: 17/958,546

(22) Filed: Oct. 3, 2022

(65) Prior Publication Data

US 2023/0048679 A1 Feb. 16, 2023

Related U.S. Application Data

(63) Continuation-in-part of application No. 17/366,150, filed on Jul. 2, 2021, now abandoned.

(60) Provisional application No. 63/047,770, filed on Jul. 2, 2020.

(51) Int. Cl.
*A61B 5/00* (2006.01)
*A61B 1/303* (2006.01)
*A61B 5/107* (2006.01)

(52) U.S. Cl.
CPC .............. *A61B 5/435* (2013.01); *A61B 1/303* (2013.01); *A61B 5/0062* (2013.01); *A61B 5/0084* (2013.01); *A61B 5/1076* (2013.01)

(58) Field of Classification Search
CPC ..... A61B 5/435; A61B 5/0062; A61B 5/0084; A61B 5/1076; A61B 5/1079; A61B 1/303
See application file for complete search history.

(56) References Cited

U.S. PATENT DOCUMENTS

| | | | |
|---|---|---|---|
| 9,655,646 B2 * | 5/2017 | Richey ................... | A61B 1/303 |
| 2005/0049509 A1 | 3/2005 | Mansour et al. | |
| 2006/0089570 A1 * | 4/2006 | Mansour ................. | A61B 8/12 |
| | | | 600/437 |
| 2011/0188716 A1 | 8/2011 | Bennett et al. | |

* cited by examiner

*Primary Examiner* — Devin B Henson
(74) *Attorney, Agent, or Firm* — Much Shelist, PC; Adam K. Sacharoff

(57) ABSTRACT

A portable system to be inserted within the birth canal for measuring dilation of a cervical region is disclosed. The system comprises a housing having a first portion sized to conform to a user's hand thereby defining a handle and a second portion sized to be inserted into the birth canal. The system includes two structured light sources configured to project a pattern onto the cervical region, a sensor, a trigger interface, a power source, and the processor configured for capturing image sensor data. The processor is configured for receiving image data from the sensor, processing the image sensor data, calculating a measurement of the dilation of the cervical region, and transmitting the data. The processor will transmit the data onto the display, presenting the measurement of dilation as well as a visual representation of the measurement.

19 Claims, 12 Drawing Sheets

SECTION A - A

BB-C

BB-B

BB-A

BB-D

5 – 6 CM Dilated

GO TO HOSPITAL!

910 — User activates light

920 — Processor receives input to activate lights

930 — Processer sends signal to activate lights

940 — Lights project pattern

950 — Sensors capture pattern

960 — Processor receives sensor data

970 — Processor uses preprogrammed logic to determine actual measurement

980 — Processor sends data to generate graphical display

APPARATUS, METHODS, AND SYSTEMS FOR MEASURING CERVICAL DILATION USING STRUCTURED LIGHT

CROSS-REFERENCE TO RELATED APPLICATIONS

This application is a continuation-in-part application claiming the benefit of U.S. Non-Provisional patent application Ser. No. 17/366,150 filed Jul. 2, 2021 and titled "DEVICE AND METHOD FOR MEASURING CERVICAL DILATION" which claims the benefit of U.S. Provisional Patent App. No. 63/047,770 titled "DEVICE AND METHOD FOR MEASURING CERVICAL DILATION" and filed Jul. 2, 2020, and the subject matter of which is incorporated herein by reference.

STATEMENT REGARDING FEDERALLY SPONSORED RESEARCH OR DEVELOPMENT

Not applicable.

INCORPORATION BY REFERENCE OF MATERIAL SUBMITTED ON A COMPACT DISC

Not applicable.

TECHNICAL FIELD

The present disclosure relates biomedical devices in the field of obstetrics, and more specifically to the field of devices for measuring the dilation of a cervix during pregnancy.

BACKGROUND

Cervical dilation is the most important indicator of labor onset and progression. The cervix is typically 2 to 3 centimeters in length (about 1 inch) and roughly cylindrical in shape, which changes during pregnancy. The cervix is located at the back of the vagina and is not directly visualized, requiring the use of a speculum inserted into the vagina to examine the cervix. During labor, the cervix opens to accommodate the passage of baby's head into the vagina, which is around 10 centimeters (cm) dilated for most term babies. If the cervix is not dilated, a woman is not in labor. But if her cervix is opening at a steady, regular rate, the she is in active labor and getting closer to delivering her baby. Here are the problems with the existing technology.

Digital exams are the standard of care to measure cervical dilation. Digital exams are poorly reproducible and time consuming for the clinician; and they are uncomfortable for the patient. A digital exam is performed during labor by the insertion of a gloved finger into the vagina and cervix of a pregnant woman to determine how much the cervix has dilated. Disadvantages of digital examination include discomfort, severe bleeding, and increased anxiety of pregnant women as well as potential health complications with the newborn upon delivery. Studies have shown that digital cervical examinations increase the risk of vaginal bacteria entering the cervix and the uterus which may cause harm to the newborn. Increased amounts of certain bacteria can be very concerning to women who have ruptured fetal membranes. Harmful bacteria may enter these membranes and cause inflammation around the fetus. During childbirth this bacteria may be passed along to the baby and cause pneumonia or other diseases. A research study examined 35 pregnant women and found that 28 of these women had nearly double the amount of vaginal bacteria in the cervix and uterus after digital examination. According to studies, the overall accuracy for determining the exact diameter of cervical dilation is 56.3%. Intra-observer variability (variation observer experiences when observing the same material more than once) for a given measurement is estimated at about 52%.

Another currently known way of measuring the dilation of the cervix is by using a mechanical cervimeter. For example, a mechanical cervimeter may be a caliper-type mechanical cervimeter with an integrated ruler. Such devices have been regularly used since 1956. However, these mechanical cervimeters are inaccurate for measuring dilation greater than 7 cm, lack a recording module, are invasive, and comprise a heavy metallic structure that can interfere with the dilation during measurement.

Similar to mechanical cervimeters, electromechanical, and electromagnetic cervimeters have also been developed and used since the mid-1950's. These add integrated sensors to convert continuous system movements into electrical signals that can be read and recorded. Electromechanical cervimeters are designed similarly to mechanical cervimeters with the addition of sensors used to convert the system movements into electrical signals, which are then read and recorded by the physician. A caliper type cervimeter was developed in 1985 by Richardson et al and further improved by Zahn and Ostarek. This device would clip onto the cervix with arms arranged to convert the angular aperture directly to an electrical signal by use of a dilation-measuring strip attached to the arms. The issues presented with this device occurred because of the lack of reliability of the clips to stay on and the inaccuracy of the angular conversion. These inaccuracies lead to errors that can further promote premature childbirth.

Electromagnetic cervimeters are designed to attach induction coils to opposite sides of the cervix creating a magnetic field. This magnetic field allows calculation of the distance across the two coils providing an estimate of the cervix dilation. The problem with electromagnetic cervimeters is the inaccuracy and inefficiency of the device. Electromagnetic cervimeters presented no advantage over digital examination, and frequently would slip off the cervix making the patient uncomfortable and having to start the process over.

Ultrasound cervimeters are another class of cervimeters and have been used since the 1970's. These devices employ ultrasound (US) transducers to measure cervical dilation. Cervical length (CL) by transvaginal ultrasound (TVUS) is routinely used to predict preterm labor, it is also used to predict spontaneous labor in prolonged pregnancies and in the predication of successful labor induction. Ultrasound imaging uses high frequency sound waves to form an image of the inside of your body. Ultrasound probes, called transducers, will transmit sound waves into the body and record the waves that echo back. Challenges presented by the ultrasound image include inaccurate presentations called artifacts. Artifacts are presented on the display as added or omitted objects, or are of improper location, size, or length compared to the true anatomical feature. This may cause confusion or errors in examinations.

Researchers at Duke University have developed a probe insertable within the vagina to view and detect cervical cancer. The device is sterilizable and re-useable, and comprises a light source and a camera having a zoom feature for enlarging the viewing field. However, the device is not configured nor capable of measuring dilation of a cervix.

While multiple tools have been conceived and developed over the years, nothing has gained traction to replace digital exams. Moreover, many women close to the end of their pregnancy, aren't able to tell the difference between early labor and active labor, let alone how much their cervix has dilated. The early stage of labor is the longest stage and some may say the most painful. This is when contractions first begin. For first time mothers this pain can be so unbearable the only solution in sight is to go to the hospital and be cared for by medical professionals. However, in some cases women will be sent home if they arrive too early; to a mother, being sent away can be frightening and stressful. Many women who are sent away end up giving birth in undesirable places with little knowledge of what they should be doing. Doctors take into consideration numerous factors when deciding if patients will be sent home including if the pregnancy is at high risk as well as if fetal heartbeat patterns are reassuring, and the cervical dilation. This is asked of the patients in order to conserve resources and prioritize those who are in active labor. It is important to reduce false labor visits as much as possible in order to conserve associated resources, reduce unnecessary costs, and reduce stress on the expecting mother and their physicians. Patients should be able to accurately measure their own cervix in a home environment with minimal invasiveness and interference, this would reduce the amount of unnecessary visits to the hospital along with unnecessary stress that may harm the expecting mother as well as the child.

As a result, there exists a need for improvements over the prior art and more particularly for a more efficient way of measuring the dilation of the cervix during pregnancy to determine the onset and progression of labor.

SUMMARY

A system and method for measuring cervical dilation using structured light is disclosed. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

In one embodiment, a portable system to be inserted within a vaginal channel for measuring dilation of a cervical region within the vaginal cannel is disclosed. The system comprises a housing having a first portion sized to conform to a user's hand thereby defining a handle and a second portion sized to be inserted into the vaginal channel. Within the housing there is a processor, two structured light sources, a sensor in electrical communication with the structured light sources, a trigger interface, a power source, and the processor configured for capturing image sensor data. The processor is configured for receiving image sensor data from the sensor, processing the image sensor data, calculating a measurement of the dilation of the cervical region, and transmitting graphical display data. The processor displays the measurement of dilation as well as a visual representation of the measurement. The display is disposed within the first portion of the housing.

Additional aspects of the disclosed embodiment will be set forth in part in the description which follows, and in part will be obvious from the description, or may be learned by practice of the disclosed embodiments. The aspects of the disclosed embodiments will be realized and attained by means of the elements and combinations particularly pointed out in the appended claims. It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute part of this specification, illustrate embodiments of the disclosure and together with the description, explain the principles of the disclosed embodiments. The embodiments illustrated herein are presently preferred, it being understood, however, that the disclosure is not limited to the precise arrangements and instrumentalities shown, wherein.

DETAILED DESCRIPTION

Figure 1:
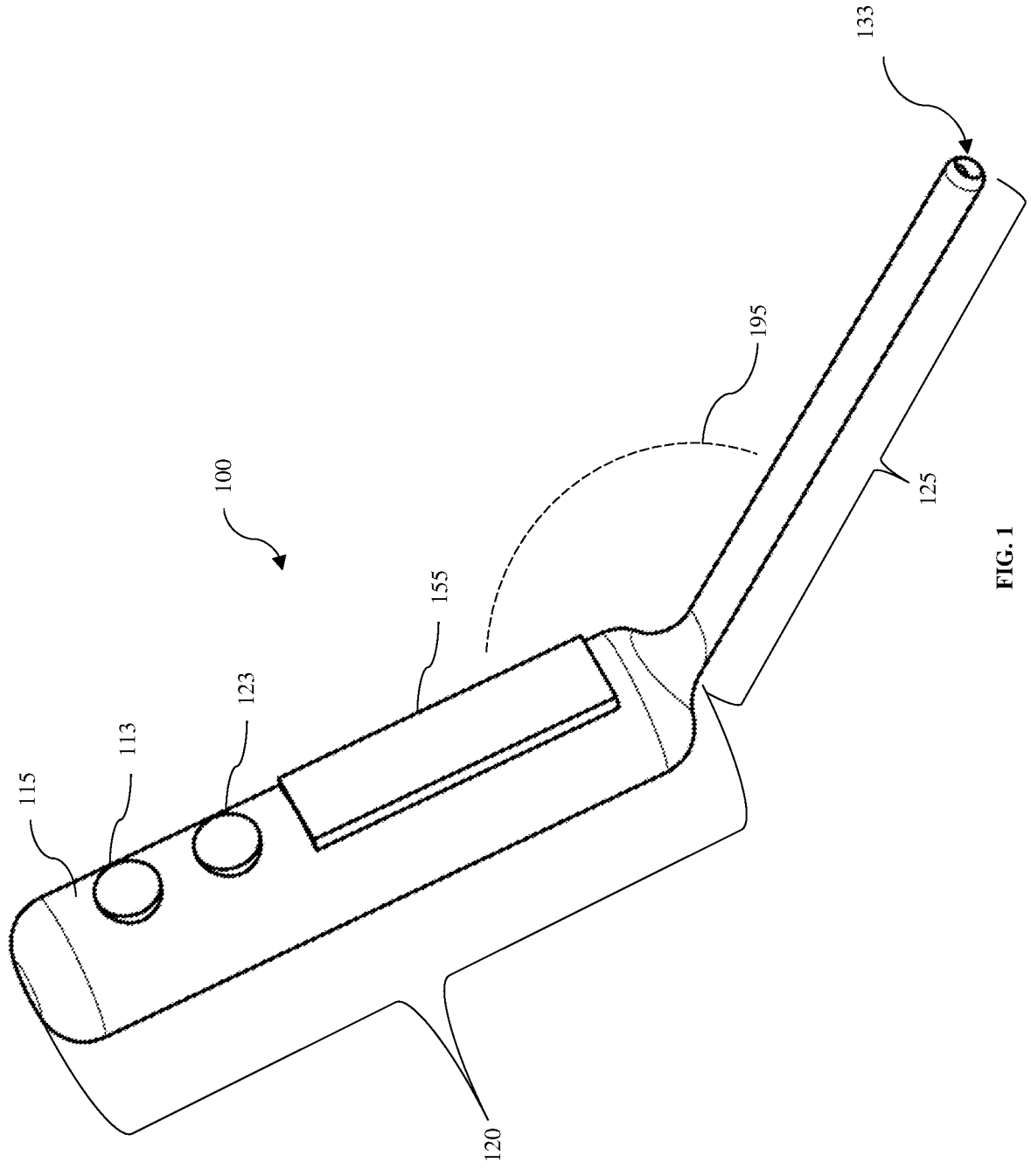
FIG. 1 is a perspective view of a system for measuring cervical dilation, according to an example embodiment.

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions, or modifications may be made to the elements illustrated in the drawings, and the methods described herein may be modified by substituting reordering or adding additional stages or components to the disclosed methods and devices. Accordingly, the following detailed description does not limit the disclosed embodiments. Instead, the proper scope of the disclosed embodiments is defined by the appended claims.

The disclosed embodiments improve upon the problems with the prior art by providing a portable device and method for accurately measuring cervical dilation. As mentioned above, there is a need for accurate and reproducible cervical dilation measurements free from human error and variability to determine the onset and progression of labor. There is an unmet need for a reliable way to measure cervical dilation to monitor labor progress. Early detection of preterm cervical dilation would allow intervention; reducing associated resources, costs and mortality related to preterm labor and premature births. Moreover, a device that can used by a patient in a home environment, can help reduce false labor visits, thereby reducing associated resources, costs, and stress can be advantageous to expectant mothers and their physicians, as well as the prenatal health care providers and industry.

The disclosed device utilizes two structured light sources to project a pattern, created from a plurality of dots, onto the cervical region. A camera then captures and communicates the image sensory data to the processor where the measurements may be calculated. The use of structured light when measuring cervical dilation is highly beneficial considering the accuracy of this method as compared to present systems and methods of cervical examination. Eliminating the possibility of human error is always beneficial, especially in the medical field. This device being minimally invasive, portable, and accurate provides improvements over the prior art.

By accurately measuring cervical dilation, with minimal invasiveness and interference, the subject device and methods can address certain problems previously identified for cervical dilation measurements. Resultant advantages provided by the subject invention, include, but are not limited to, facilitation of monitoring of cervical dilation to track labor progression for detecting and intervening in preterm labor, reducing false labor visits and reducing inductions or Caesarean (C-Section) rates. The ability to detect and intervene in preterm labor would have a positive impact by reducing waste of hospital resources, reduce costs such as unnecessary use of staff and beds, and potentially increase the health, safety, and well-being of a mother and to-be-born child.

Referring now to the Figures, FIG. 1 is a perspective view of a portable system 100 including a housing 115, which contains a housing first portion 120 and a housing second portion 125, a power button 113, a capture button 123, a capture module 133, and a display 155, according to an example embodiment. In a preferred embodiment the shape and size of the housing first portion is sized to conform to a user's hand resembling a handle. The housing second portion may be disposed at an angle 195 approximately between 90 degrees and 180 degrees relative to the first portion and is sized to be inserted into the vaginal channel to capture the dilation of the cervical region. However, in other embodiments, the housing may vary in size and may appear to be shaped differently. The housing may be manufactured from a variety of different processes including extrusion, casting, molding, forming, 3D printing, CNC machining, etc., furthermore, may be formed from a single piece or several individual pieces joined or coupled together. The housing may also be comprised of metallic materials or polymeric materials such as polycarbonates like Acrylonitrile butadiene styrene (ABS plastic), Lexan™, and Makrolon™. The housing of the device is preferably made from biocompatible, sterilizable and reusable materials, and may include an outer sterile cover which is removable and replaceable for multiple uses of the device. The sterile cover can be transparent to minimize interference with imaging. However, other materials and processes may also be used and are within the spirit and the scope of the present invention.

The display 155, may display the measurement and the visual representation of the cervical region. The display is in electrical communication with the power source, and the processor. Medical displays are commonly in the form of a monitor having special image-enhancing technologies, while being in compliance with the standard set forth by Digital Imaging and Communications in Medicine (DICOM). Examples of displays that may be used in the present invention include surgical grade displays, medical grade LCD displays, small touch screen solutions, etc. Other displays may be used within the spirit and scope of the disclosure.

The power button and the capture button appear circular in the present embodiment, however in other embodiments the buttons may appear differently. For example, the buttons size may appear smaller or larger, the buttons shape may not be circular, and the orientation of the two buttons may be different than what is shown is FIG. 1. The buttons may be in the form of a flush push button switch, an extended push button switch, a slide switch, a rocker switch, pressure switches, etc. Other types of buttons or switches may also be used as a power button and a capture button and are within the spirit and the scope of the present invention. The buttons may be manufactured from a variety of different processes including extrusion, casting, molding, forming, 3D printing, CNC machining, etc., furthermore, may be formed from a single piece or several individual pieces joined or coupled together. The buttons may also be comprised of metallic materials or polymeric materials such as polycarbonates like Acrylonitrile butadiene styrene (ABS plastic), Lexan™, and Makrolon™. However, other materials and processes may also be used and are within the spirit and the scope of the present invention. The capture button may be configured to engage the capture module (discussed below) acting as a trigger, to turn on the structured light source(s), then capture the image of the projected shape and/or pattern using the sensor, then processing the image to determine measurements of the cervical region based on deformations in the captured image. Such determined measurements may be displayed on the display as a numerical measurement or may be displayed as a graphical visual aid, such as a chart or diagram. In some embodiments, the processor may display, on the display, a prompt for the user based on the measurements, where such prompt is a medical advice or recommendation based on the measurement. For example, the device may display "go to the hospital", "seek medical attention", and/or "minimal dilation, take measurement again in one hour". Other prompts are within the spirit and scope of the disclosed invention.

The capture module may include a structured light source and a sensor, however in other embodiments the capture module may include multiple structured light sources and multiple sensors as well as a variety of components. The structured light source comprises a diffractive optical element which allows the light source to project a shape and/or pattern onto the cervical region. The sensor then captures a series of images, either automatically and/or using the capture button. The image captured by the sensor is analyzed by the processor as image sensor data of which the processor measures the deformation of the shape and/or pattern on the cervical to determine the dimensions of the cervical region, such as dilation and/or depth.

Figures 2, 2A:
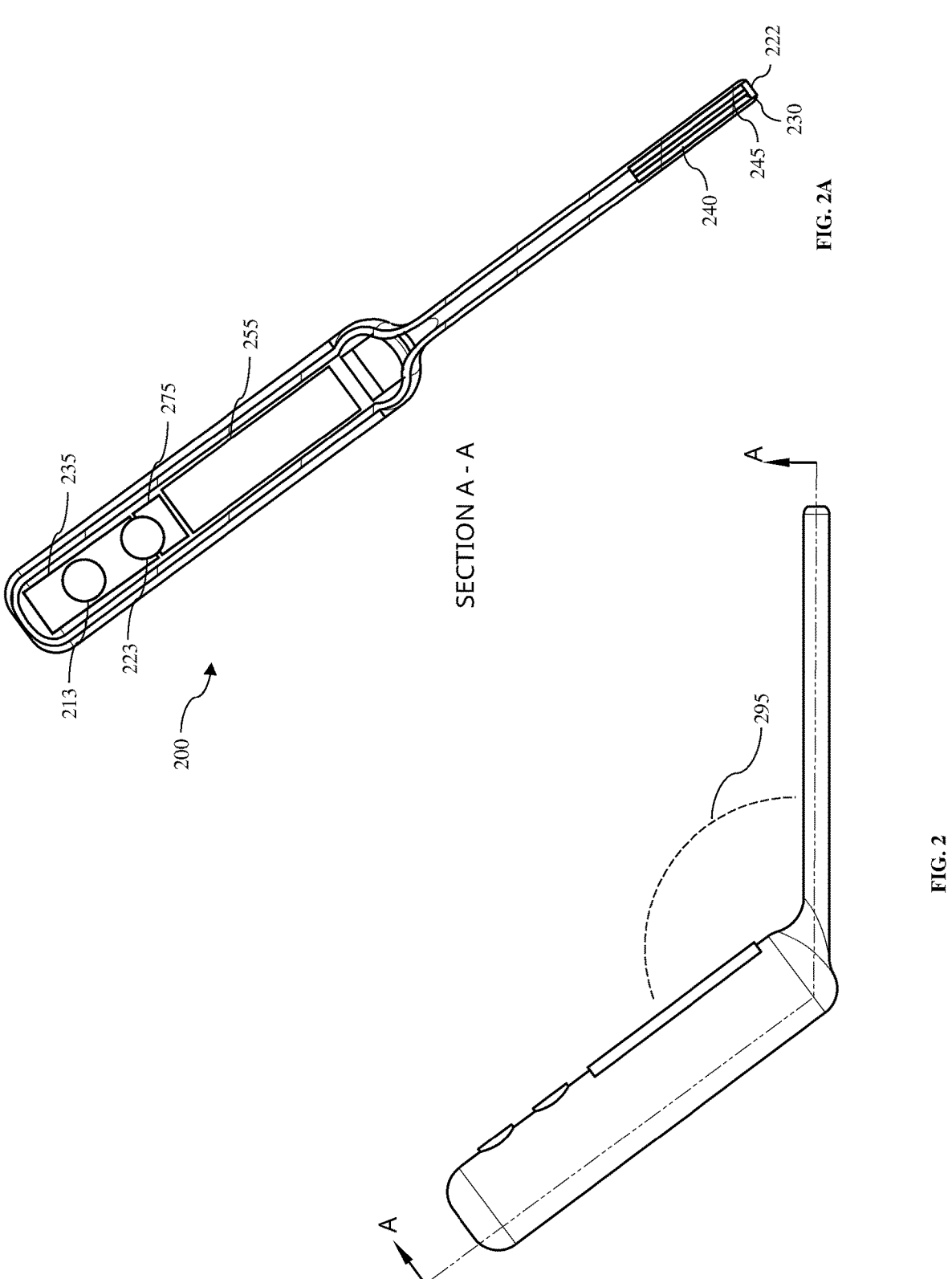
FIG. 2 is a side view of the system, according to an example embodiment.
FIG. 2A is a cross-sectional view of FIG. 2 illustrating the components of the system disposed within the housing, according to an example embodiment.

FIG. 2 is a side view of the device illustrating an angle 295 between the first and second portions of the device. Cross section A-A is also depicted in this side view which is further detailed in FIG. 2A. The angle 295 between the first portion and the second portion of the device may be between 0 degrees and 360 degrees. However, the angle between the first portion and the second portion is generally between 90 degrees and 180 degrees, and ideally approximately 135 degrees. The angled tilt of the handle in comparison to the probe, or second portion of the device, is more comfortable for the user for self-examination. Because the handle is tilted, the user can see the screen of the device and see the graphical displays and measurements. In certain embodiments, the device takes real-time measurements of depth to the cervical opening and displays the distance to the cervical opening on the display in real-time. This allows the user to safely insert the probe (second portion) into the birth canal without inserting the device too deep as to harm, or potentially harm, oneself and/or the prospective child.

FIG. 2A is a cross sectional view of the device across section A-A. FIG. 2A illustrates a portable system 200 having a first portion 220 (the handle) and a second portion 225 (the probe). The first portion includes a power button 213, a capture button 223, a power source 275, a processor 235, and a display 255. The first portion is sized to conform to a user's hand thereby defining a handle. The second portion of the device includes a structured light source 240, a sensor 245, a camera 230, and a window 222. The second portion is sized to be inserted into the vaginal channel and/or birth canal, and for capturing the dilation of the cervical region. Thus the shape of the second portion is generally tubular and/or a phallic shaped to allow the user to easily insert the device into the birth canal. During insertion, the second portion may be coated with a lubricant, such as water based lubricants, silicone based lubricants, and/or oil based lubricants, to facilitate the insertion of the device within the birth canal. In some embodiments, the device may include at least one disposable probe cover configured to receive the probe prior to administration into the birth canal. The disposable cover provides a sanitary cover to prevent germs, viruses, and bacteria from being instilled into the birth canal, which may cause irritation and/or infection. The disposable probe cover may be made of non-toxic, medical grade plastics and/or food grade paper, and high elastic materials to be sized to fit a variety of probes of different dimensions.

The processor 235 is configured for receiving the image sensor data, processing the image sensor data, calculating the measurement of the dilation of the cervical region, and transmitting the graphical data containing the dilation, to the display 255. The processor is further configured for generating a visual representation of the cervical region and displaying at least one of the measurement of the dilation, and the visual representation of the measurement. Processing the image sensory data includes determining at least two distortion points in the unitary pattern of light when it is projected onto the cervical region. Calculating the measurement of dilation includes determining the distance between at least two distortion points in the unitary pattern of light. The processor is in electrical communication with the sensor and the power source. The trigger interface is positioned within the first portion and is in electrical communication with the processor, the camera, the power source, and at least one of the structured light sources. The processor processes the image sensor data to locate and identify the cervical region based upon the distortion of light projected onto the region and/or the depth of the device within the birth canal. The processor then calculates the cervical region size and opening using the identified cervical region and the distance measurement to scale the image sensor data in the cervical region.

The power source 275 is positioned within the first portion and is in electrical communication with the processor, the camera, the display, and at least one of the structured light sources. The power source may be distributed from the electrical power grid, such as an electrical outlet, energy storage devices such as standard dry cell batteries, generators, alternators, solar power converters, etc. Other power sources may also be used and are within the spirit and the scope of the present invention.

The sensor 245 is positioned within the housing, and is configured for capturing image sensor data. The sensor is in electrical communication with the first structured light source, the power source, and the processor. An imaging sensor is used to obtain a 2D or 3D image from a structured light illumination. If the subject is non planar, the structured light pattern is distorted. The goal of structured light 3D surface imaging techniques is to replicate the 3D surface by using various structured light principles and algorithms to create a relationship between an imaging sensor, a structured light source, and a subject surface. An example of a common imaging sensor used in the medical field is known as Complementary Metal Oxide Semiconductor (CMOS) Imaging Sensors (CIS). These sensors are minimally invasive, they possess high resolutions, low sensitivity, low power consumption, and faster frame rates.

The camera 230 is positioned within the second portion, and is configured for capturing and communicating image sensor data to the processor. The camera is in electrical communication with the power source, the processor, and the trigger interface. The camera is a type of imaging sensor, as stated above, a camera may be used to obtain a 2D or 3D image under structured light illumination. If the surface in the scene is non planar, the structured light pattern is distorted. The goal of structured light 3D surface imaging techniques is to replicate the 3D surface by using various structured light principles and algorithms to create a relationship between an imaging sensor or camera, a structured light source, and a subject surface. As mentioned above, the most common imaging sensor, or camera, used in the medical field is known as Complementary Metal Oxide Semiconductor (CMOS) Imaging Sensors (CIS). These sensors are very beneficial because of features being minimally invasive, having high resolutions, low sensitivity, low power consumption, and faster frame rates. Sensor and structured light source are disposed within the probe proximate to the terminating end of the probe having the window or opening. The window or opening allows the structured light source and sensor to have an unobstructed projection or view of the subject matter, namely the opening of the cervical region to measure dilation. It is important that the opening or window is unobstructed because the sensor captures the image, of which, the processor determines measurements based on distortion in the image. The image sensor captures the brightness of the shape or pattern of light projected onto the cervical region. The image sensor data comprises RAW data, which is data comprising the light intensity of various points of the image. To actually visualize the image as a graphical representation that may be viewed on the display for example, the processor must convert the light intensity data into an image file such as a .png, .jpeg, and .tiff., etc. to visualize the image captured. The light intensity data comprises the light was projected onto the cervical region. Portions of the cervical region that are closer to the camera may appear at a brighter intensity whereas the cervical opening may be distorted or a darker intensity. As such, the processor determines the differences in the light intensity and takes a measurement between two points as to measure the dilation of the cervix.

The structured light source is located in the second portion of the device near the sensor and/or camera. Structured light 3D scanning works by projecting a pattern onto an object, then allowing a camera to analyze the drop offs in the pattern and convert these discrepancies to depth values used to form a 3D image. Structured light scanning may use white light being easily accessible, or blue light being most accurate efficient when minimizing effects of reflections and transparency. Color structured light is also commonly used for measurements. To generate a stripe pattern on the subject, a single light source must pass through a spatial light modulator, or two laser beams must intersect. In some embodiments the sensor may have a light source on itself in addition to the individual structured light source, thus forming two beams of light. Preferably, LED illuminators provide white light, or can provide light of specific wavelengths, such as light within the infrared wavelength range. More preferably the LED illuminators can generate light of varying wavelengths, including white light or infrared light, and can be adjusted by the user as needed for the desired image being produced.

The window 222 is generally open and unobstructed, however, it may, in certain embodiments, comprise a transparent lens or film over the surface acting as a protective layer to prevent fluids and/or bacteria, dirt, and germs, from entering the probe and damaging the components. However, it is important to note, that even the lightest imperfections in the transparent film or lens may distort the light projected on to the cervical region causing inaccurate measurements and/or measurements of greater variability. Therefore, in other embodiments, the window may have no lens or film allowing the structured light source to interact directly with the subject. Ideally, the window 222 is an unobstructed opening to the sensor and the structured light source.

Figures 3, 3A, 3B, 3C, 3D:
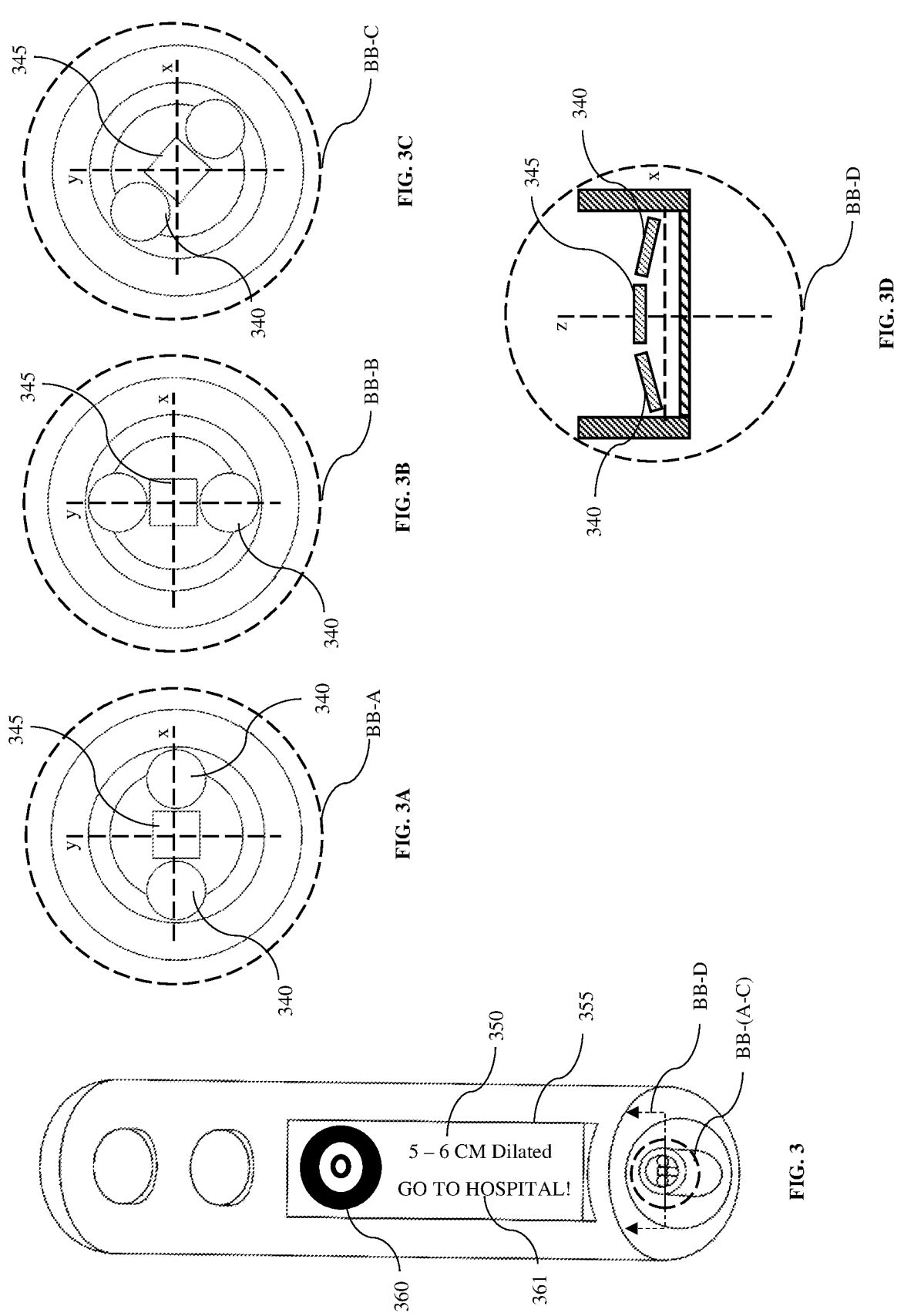
FIG. 3 is a front perspective view of the system, according to an example embodiment.
FIGS. 3A is a detailed view of FIG. 3A, according to a first example embodiment.
FIGS. 3B is a detailed view of FIG. 3A, according to a second example embodiment.
FIGS. 3C is a detailed view of FIG. 3A, according to a third example embodiment.
FIGS. 3D is a cross-sectional detailed view of FIG. 3A, according to a fourth example embodiment.

FIG. 3 is a front view of the device according to an example embodiment. The figure is an exemplary embodiment of the display 355, on the housing first portion, having a visual representation 360 of the measurement 350 of the dilation of the cervical region. The visual representation 360 may be a diagram, chart, illustration, and or the image senor data converted into a visualized image in a processable format, such as JPEG, PNG, TIFF, PDF, etc. As shown, the visual representation 360 is a target shaped diagram having concentric rings to emulate the pattern projected by the structured light source. The display may highlight certain rings or regions of the diagram to illustrate in layman's terms, by way of example, the extent of dilation of the cervical region.

Figure 3F:
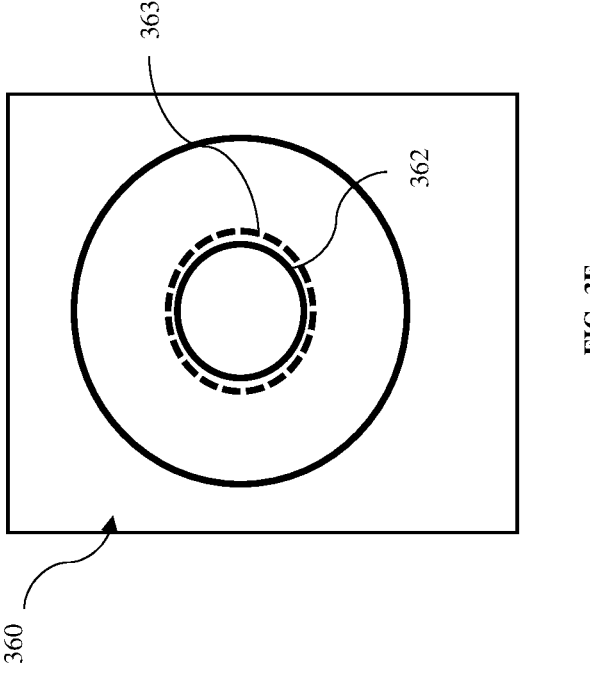
FIGS. 3E and 3F are diagrams of graphical displays that may be used, according to an example embodiment.
Figure 3E:
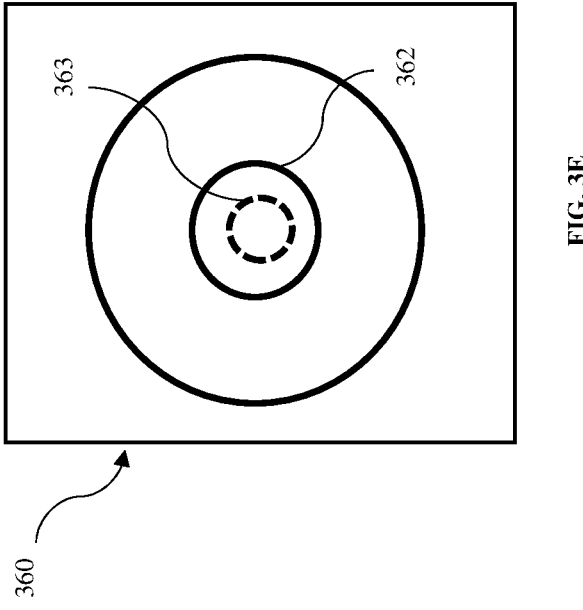

FIGS. 3E and 3F illustrates a graphical representation of a minimum dilation of the cervix or threshold dilation 362 that a physician may advise the patient seek hospital care, in reference to a graphical representation of an actual recorded dilation 363 of the cervix that may be obtained when a patient uses the device. The minimum dilation, also referred to as the threshold, is represented by the solid line labeled 362. The actual dilation of the cervix is represented by the dotted line labeled 363.

The latent phase of labor is the first stage of labor. During this stage, the cervix begins dilating and the mother begins experiencing contractions that are not yet strong or regular. Studies have shown that first time mothers experience a longer latent phase than women who have already experienced child birth. The cervical dilation during this stage may reach up to 4 cm. This stage is where many women experience false labor and should go to the hospital or seek medical care. A woman is considered to be in active labor when the cervix dilates to 5 or 6 cm with contractions becoming stronger and more regular. In one embodiment, the threshold dilation that should be seen before going to a hospital. However, there is no strict rule of when to seek professional attention when giving birth. As mentioned before, first time mothers tend to experience long stages of labor as their body is going through changes its never experienced before. Some women have a low pain tolerance forcing them to require a sedation to ensure they make it through the final stage of labor.

There are many factors that may influence the timing of the stages of labor. It is best to seek advice from the medical professional assisting you throughout a pregnancy. Most pregnant women entering the first stages of labor have no idea how much their cervix is dilated. The claimed invention, including the graphical representations shown in FIGS. 3E and 3F may be extremely helpful when determining the right time to go to the hospital is and when the expecting mother can stay home. This device does not require any significant medical knowledge before use which is a major benefit of the design. The expecting parents may operate it, a midwife may operate it, etc. The threshold measurement may be pre-programed into the preprogrammed logic of the processor or may have an option to input a specific measurement into the device using the interface. For example, if a doctor advised the mother to come to the hospital early when the cervix begins dilating, then the device user can input 2 or 3 cm as the threshold, notifying when the woman need to make her way to the hospital. After the threshold measurement has been programmed into the device, the processor may send a signal to the graphical display to the display a graphical representation of the threshold measurement on to the display 360. Additionally, after the measurements are calculated using the preprogrammed logic input into the processor 735, the processor may send data to the display in order to display the actual measurement as a graphical representation relative to the threshold measurement. While rings have been used to display the actual measurement relative to the threshold measurement as illustrated in FIGS. 3E and 3F, other embodiments may be used to display the actual measurement vs. the threshold measurement such as a plus vs. minus sign; different colors (such as red or green); GO vs. NO GO etc. Additionally, additional information may be programmed into the process to display different information if the actual measurements are a certain amount greater than the threshold measurement. For example, if the actual measurement is 5 cm over the threshold measurement (or some other amount that would indicate an emergency, then the system may display a warning (such as using the term "911" or "SEEK IMMEDIATE ATTENTION") that would indicate to the user that there is a medical issue and to seek immediate care.

The display may also include, a prompt 361 such as a message directing the user to take an action, such as go to the hospital or to stay home. The device may be programmed to make a sound or read a statement when the cervix is dilated a certain amount.

The display may provide the user with messages and/or notifications regarding medical diagnosis, such as dilation, or advice, such as when to go to the hospital when the measured dilation reaches a certain predetermined dilation, such as 5 cm for example. Such prompt 361 is dependent on the measurement of dilation. Prompting the user to stay home when dilation has not progress enough may free up hospital resources and prevent crowded wait times and/or pregnancy scare. For example, a women having Braxton Hicks contractions, which are contractions in preparation for labor that are premature to labor, may make a women fell like they are in labor and need to go to the hospital. This invention would allow the woman to quickly and accurately measure the dilation of her cervix to determine whether or not to go to the hospital and whether or not it is premature to go to the hospital.

Moreover, the display may provide the exact measurement of dilation, as shown by measurement 350 on the display. It is understood that in other embodiments, the processor may transmit, via Bluetooth® or my other transmission means, the image sensor data that has been processed to a visual representation and measurement, to an external display, such as a smartphone or other computing device. The external computing device may be configured to display a plurality of information dependent from the image sensor data, for example, the visual representation, the measurement, the depth, the raw data, the actual image captured by the sensor, dilation projections, etc. In other embodiments, such detailed information may be displayed on display 355 on the handle of the device.

FIG. 3 includes representations of the detailed section view BB-(A-C) of which example embodiments (represented by BB-A, BB-B, and BB-C in FIGS. 3A through 3C) of the capture module having the structured light source and sensor are shown in FIGS. 3A thought 3D. FIG. 3D is an example embodiment of the capture module across cross-section BB-D of FIG. 3.

FIGS. 3A-3C illustrate the structure light source being offset from the sensor. Structured light is generally used by having at least one structured light source. With one structured light source, the device may have a spatial light modulator to separate the structured light into a preformed pattern or array of light. However, generally, a single beam of light having uniform intensity is not enough to capture depth. Therefore, at least two structured light sources should be used to measure distance of the cervical opening as well as the depth to the cervical opening. The structured light source projects a finely calibrated pattern, such as those shown and described in FIGS. 4 through 4B, onto the cervical region within the birth canal. The gradual drop off of light intensity between the spaces of the pattern allow the sensor to differentiate depth values. In one embodiment the system may include one structured light source, a sensor, and a spatial light modulator. In another embodiment, the system may include two structured light sources and a sensor. It is understood that in the latter described embodiment, one of the structured light sources may be the sensor having a light source rather than being two distinct and separate elements.

Figure 5B:
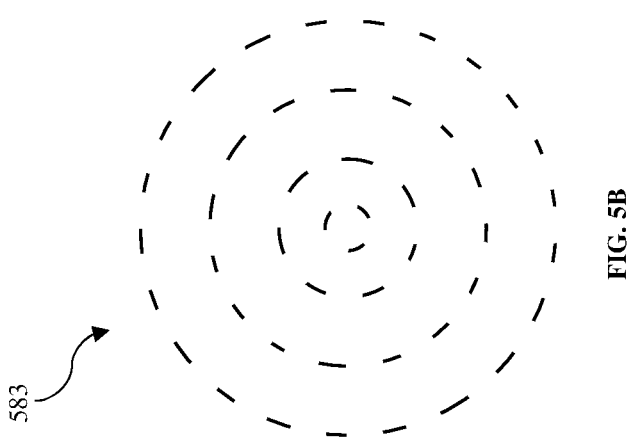
FIG. 5-FIG. 5B illustrate a unitary pattern, a first pattern, and a second pattern, according to an example embodiment.
Figure 5A:
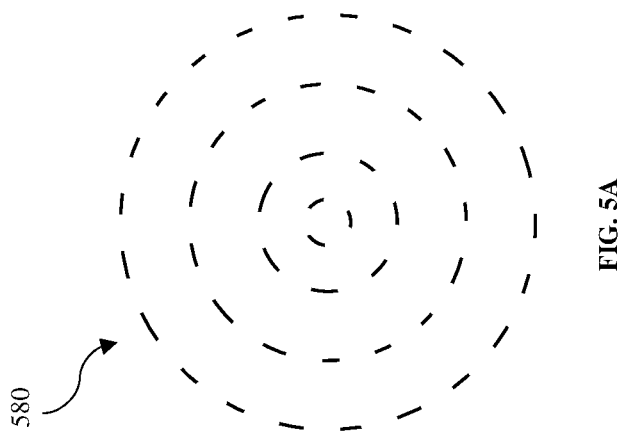
Figure 6:
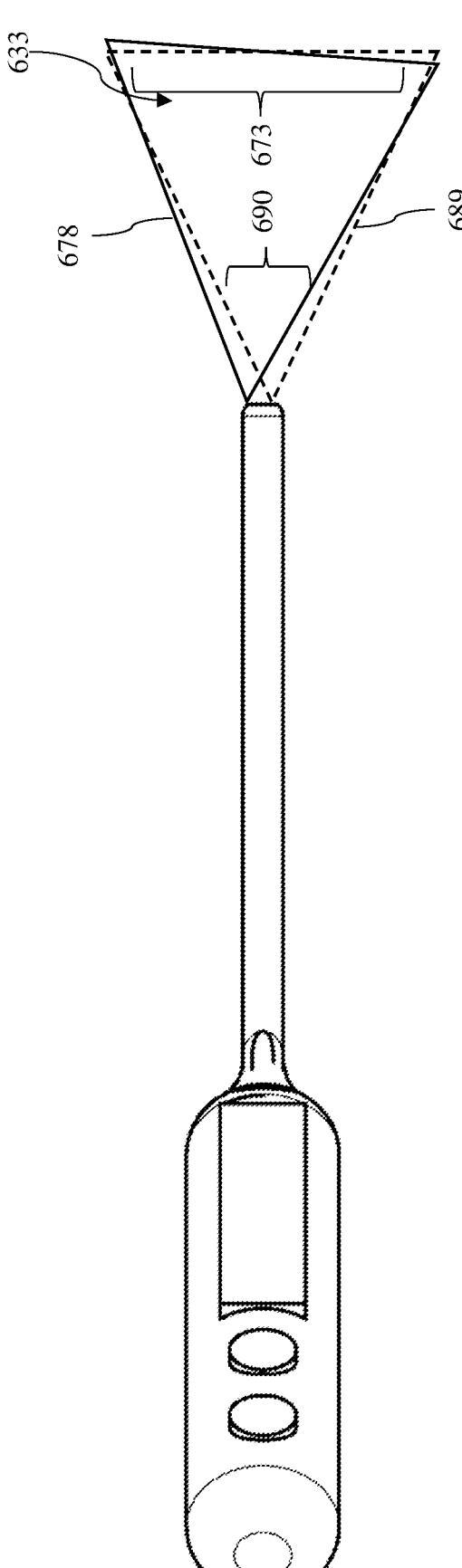
FIG. 6 illustrates a top view of the system diagraming the projection of structured light.

In FIGS. 3A through 3C, the detailed view of the capture module at the end of the housing second portion or probe is broken up into quadrants about a horizontal x-axis and a vertical y-axis. FIG. 3D shows the top view (illustrated as a cross-sectional view) of the capture module broken up into quadrants about the horizontal x-axis and an intersecting horizontal z-axis directed into the probe. These embodiments serve to illustrate the different positions the light sources may be arranged as offset from the sensor. The square shown in the middle of the embodiment represents a sensor or camera 345, while the circles on either side of the camera represent the structured light source(s) 340. In other embodiments, there may be one structured light source and one sensor or camera recording the distortion. To generate a pattern on the subject, a single light source must pass through a spatial light modulator, or two laser beams must form an intersecting pattern (such as shown in FIGS. 5A through 5B). FIG. 3A illustrates the sensor 345 horizontally offset from the structured light source(s) 340. The sensor and structured light source(s) are horizontally offset such that they encompass different regions of the quadrants on the x-axis. FIG. 3B illustrates the sensor 345 vertically offset from the structured light source(s) 340. The sensor and structured light source(s) are vertically offset such that they encompass different regions of the quadrants on the y-axis. FIG. 3C illustrates the sensor 345 being both vertically offset and horizontally offset from the structured light source(s) 340. The sensor and structured light source(s) are both vertically offset and horizontally offset such that they encompass different regions of the quadrants on the x-axis and the y-axis. FIG. 3D illustrates how the sensor and structured light source(s) may be tilted in the z-axis to create a third dimension of how the elements may be offset. It is understood that the sensor and structured light source(s) may be any combination of horizontally offset, vertically offset, and/or tilted offset. It is further understood that offset shall mean not having the same disposition as to project light at the same angle or from the same respective origin, with respect to the subject matter. To measure depth, it is important that the structured light source(s) are offset from the sensor. The structured light source(s) may have a field of view substantially aligned with each other to create a unitary pattern, however, even the slightest deviation of being offset from the sensor allows the processor to calculate the depth of the device as inserted into the birth canal. FIG. 6 further illustrates the offset angles of the structured light sources.

Figure 4:
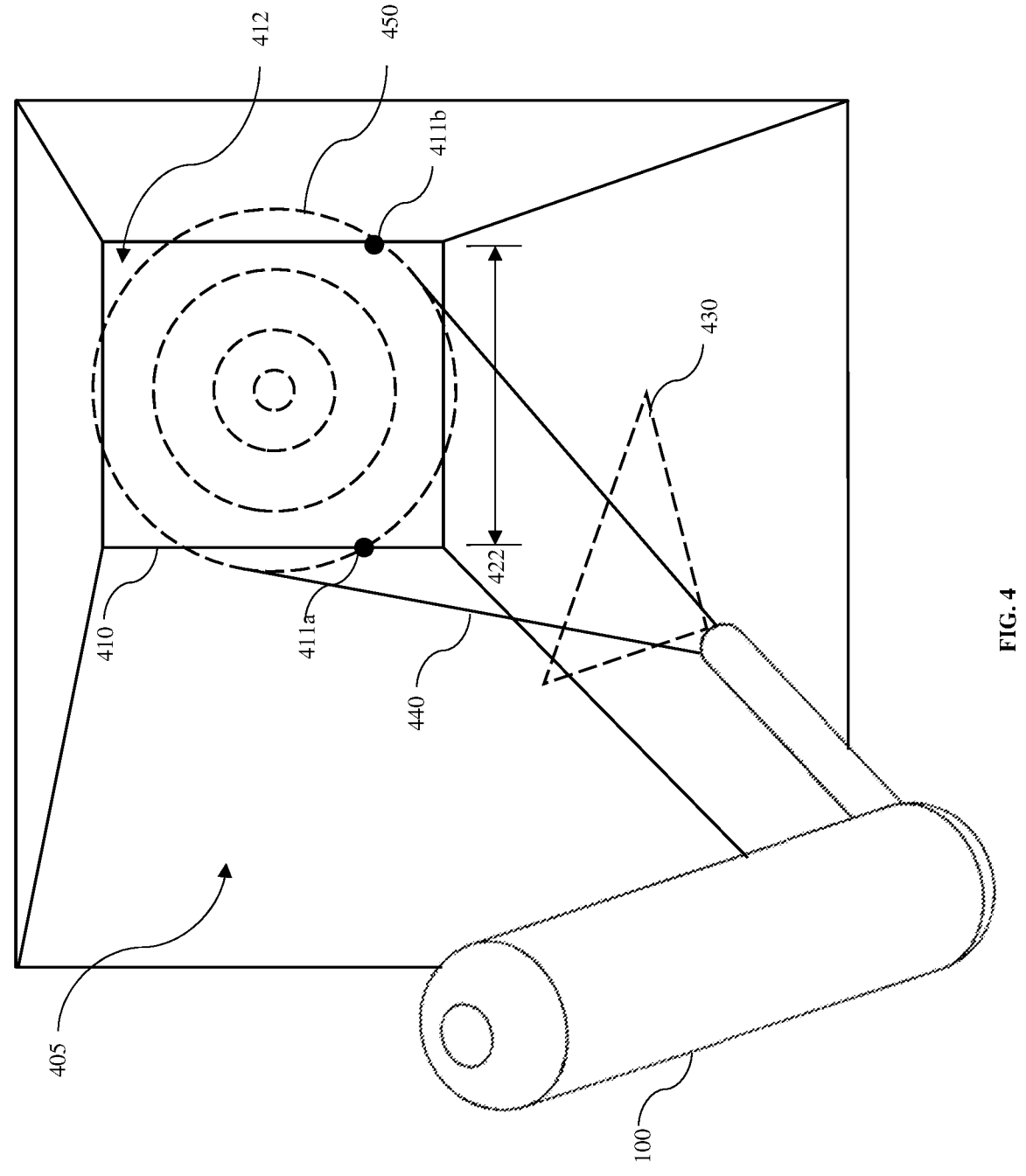
FIG. 4 is a perspective diagram illustrating the system projecting a first pattern of structured light onto the cervical region within a birth canal; according to an example embodiment.
Figure 4A:
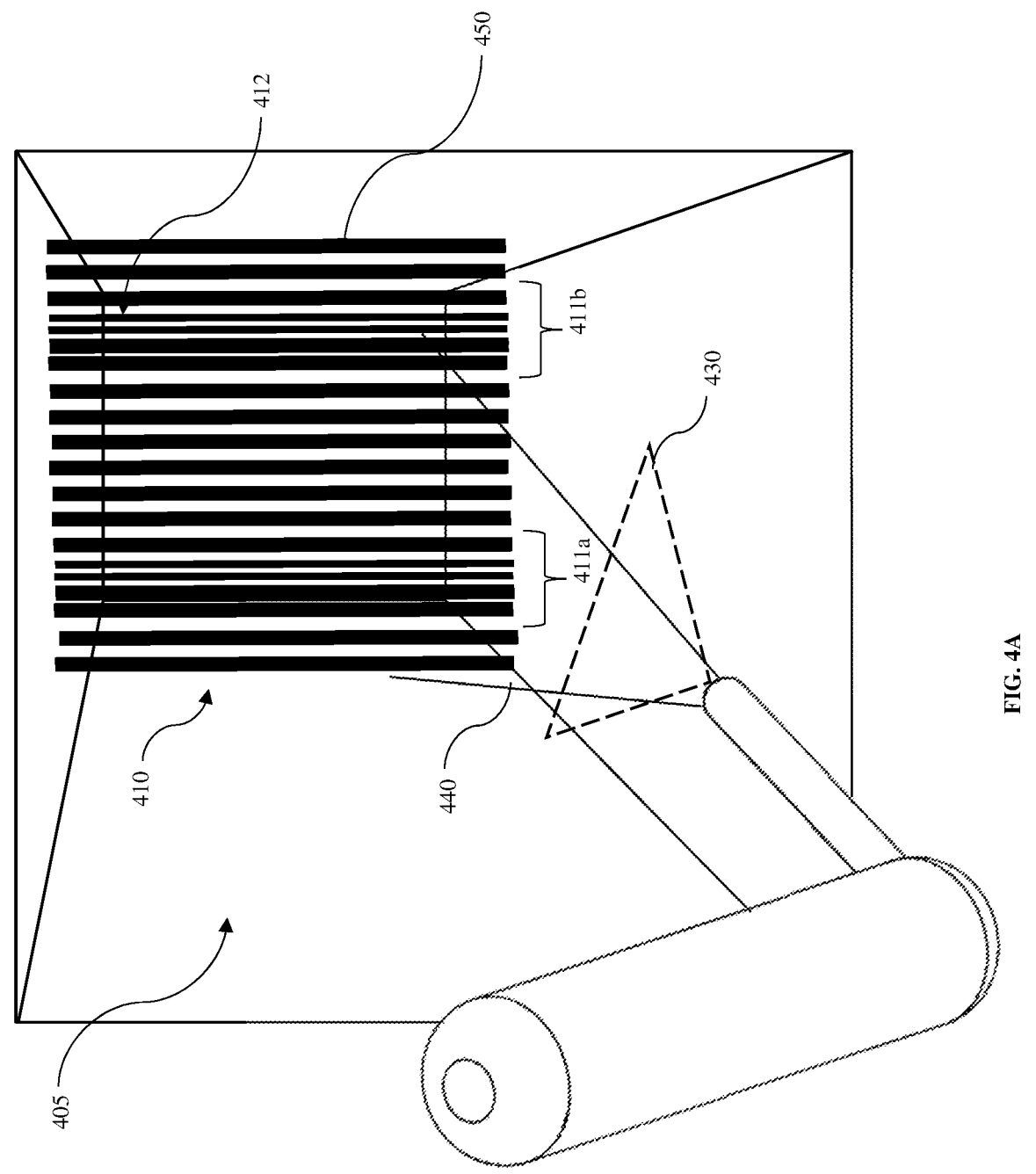
FIG. 4A is a perspective diagram illustrating the system projecting a second pattern of structured light onto the cervical region within the birth canal, according to another example embodiment.
Figure 4B:
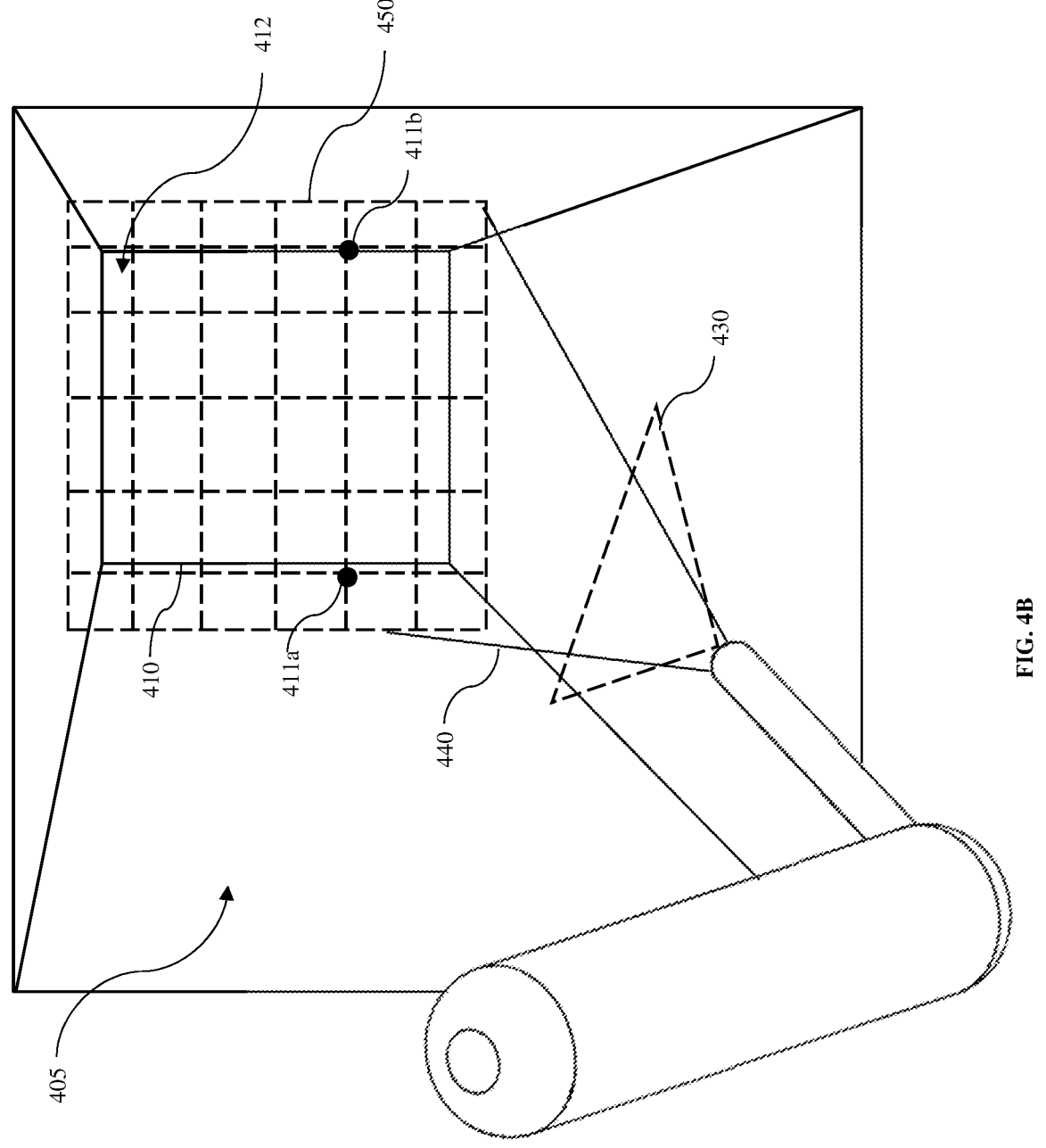
FIG. 4B is a perspective diagram illustrating the system projecting a third pattern of structured light onto the cervical region within the birth canal, according to another example embodiment.

Referring now to FIGS. 4 through 4B, a diagram device being used within the birth canal is shown according to numerous example embodiments having the structured light projecting different patterns. These figures include a representation of the device 100 disposed in an accentuated representation of a vaginal channel 405 or birth canal, a cervix 410, and a cervical opening 412. The device 100 projects, using the structured light source(s) 440, the pattern 450 on the cervical region 410. The pattern spans across a substantial portion of the cervical opening 412. The camera 430 captures an image of the light intensity on the cervical region. The processor of the device may use two points on the image that are distorted to calculate the dilation 422 of the cervical opening, such distortion points 411a and 411b, where the distortion points are on opposing sides of the cervical opening. The dilation 422 is the distance measured between the distortion points 411a and 411b. In another embodiment, the processor uses an algorithm factoring in the depth of the device, measured from the terminating end of the probe to the cervical opening, to measure the distance between the distortion points to generate the measurement of dilation.

Referring specifically now to the pattern 450 in FIGS. 4 through 4B, FIG. 4 illustrates the pattern 450 as a plurality of dots or hashes arranged in concentric rings. A concentrically arranged pattern of light may allow the measurements to be easily taken with respect to the diameter and/or radius of the ring having the distorted point, assuming that the center of the pattern is concentrically arranged with the cervical opening. In another embodiment, as shown in FIG. 4A, the pattern 450 may include a plurality of stripes, wherein the stripes become distorted on uneven surfaces, such as the around the opening of the cervical region. As shown in FIG. 4A, the opening of the cervical region creates a distortion in the pattern 450 having distorted region 411 and distorted region 411b. The light stripes may be closed together at this distortion region creating greater intensity of light as captured by the sensor forming the image sensor data. In FIG. 4B, a grid-like pattern 450 is shown being displayed on the cervical region. The processor may calculate the dilation of the cervical opening be determining the distance between distortion points on the grid. It is understood that the patterns formed by the structured light source(s) may be formed from a single light source having a spatial light modulator to create the pattern, or from a plurality of light sources forming a unitary pattern. Other patterns of structured light may be used and are within the spirit and scope of the disclosure.

Figure 5:
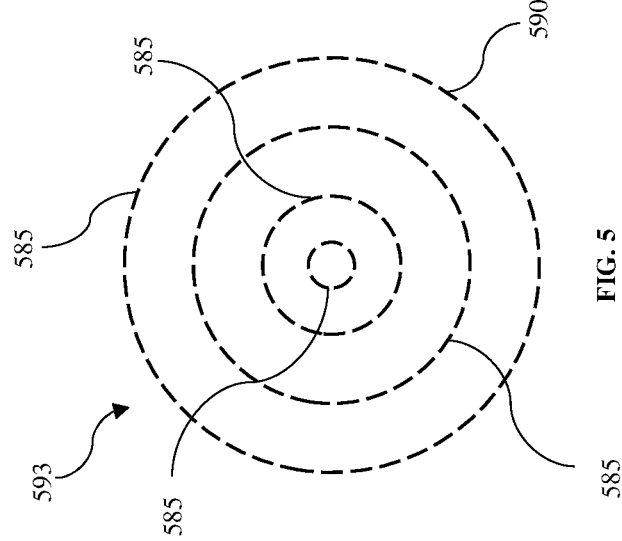

FIGS. 5 through 5B illustrate a first pattern 580 and a second pattern 583, forming a unitary pattern 593. The unitary pattern 593 is defined by a plurality of concentric rings 585 and a plurality of dots 590. The first structured light source is positioned within the second portion and is configured to emit light onto the cervical region in a first pattern containing a plurality of concentric rings, where each ring contains a plurality of dots. The first structured light source emits light onto the cervical region, or target, in the first pattern. The second structured light source is positioned within the housing second portion and is offset from the structured light source. The second structured light source is positioned within the second portion and is configured to emit light onto the cervical region, or target, in a second pattern. A unitary pattern is formed when the first pattern and the second pattern are both emitted onto the cervical region. The unitary pattern consists of the plurality of concentric rings comprising the plurality of dots. The first pattern and the second pattern overlay to define the unitary pattern.

FIG. 6 illustrates a top view of the device projecting the pattern 678 from the first structured light source and the field of view 689 of the image from the sensor. For purposes of this description, the sensor includes a second structured light source projecting a second pattern within the field of view 689. The lighted area 673 is projected onto the cervical region and is caused by the pattern 678 of the first structured light source being substantially aligned with the second pattern 689 of the second structured light source, thereby creating a unitary pattern of light on the cervical region. As illustrated, the structured light source projecting the pattern 678 is offset from the sensor having the field of view 689. The elements may be horizontally offset, vertically offset, or angled in the z-direction, being offset. As illustrated in FIG. 6, the angle of the field of view of the camera or sensor is substantially the same as the beam pattern of the first structured light source. However, because they are offset by angle 690, the processor is able to calculate the depth of the device with respect to the cervical region as well as the dilation of the cervical opening. In other embodiments, the device may contain a second structured light source separate from the sensor. In other embodiments the device may use two structured light sources, and a camera or sensor for capturing the desired content.

Figure 7:
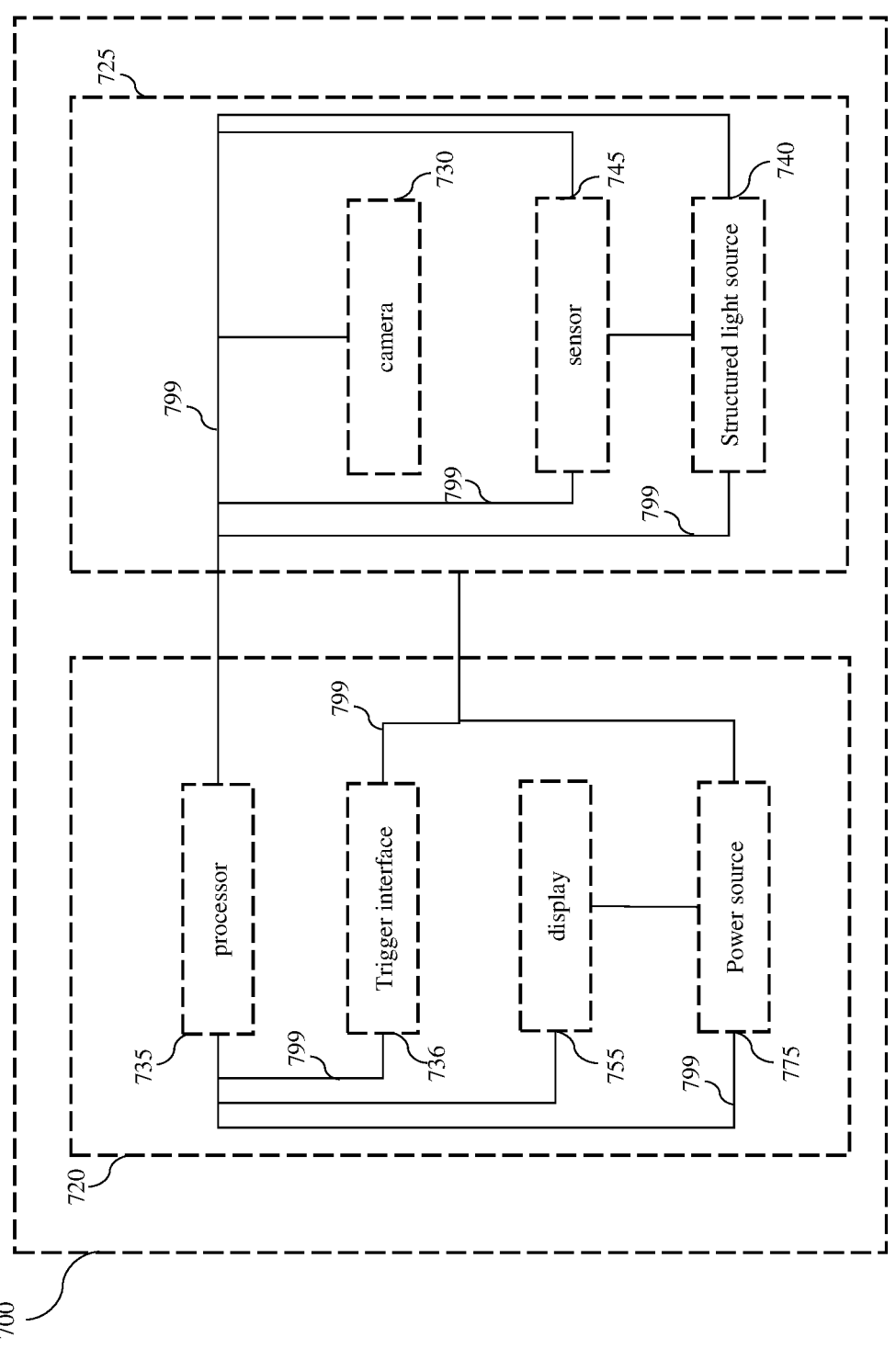
FIG. 7 is an electrical schematic illustrating the components of the system.

FIG. 7 is an electrical schematic illustrating the relation between the electrical components of the device. This schematic includes a system 700, having a first portion 720 and a second portion 725. The first portion contains a processor 735, a display 755, a power source 775, and a trigger interface 736. The second portion contains a camera 730, a sensor 745, and at least one structured light source 740. The elements are in communication with each other through electrical conductors 799, as to transfer power from the power source to the components of the system and/or to facilitate the transmission of data from the components to the processor.

The processor 735, is configured for receiving the image sensor data, processing the image sensor data, calculating the measurement of the dilation of the cervical region, and transmitting the graphical data containing the dilation, to the display. The processor is further configured for generating a visual representation of the cervical region and displaying at least one of the measurement of the dilation, and the visual representation of the measurement. Processing the image sensory data includes determining at least two distortion points in the unitary pattern of light when it is projected onto the cervical region. Calculating the measurement of dilation includes determining the distance between at least two distortion points in the unitary pattern of light. The processor is in electrical communication with the sensor, the power source, the trigger interface, the display, the camera and the structured light source.

The trigger interface 736, is positioned within the first portion and is in electrical communication with the processor, the camera, the power source, and at least one of the structured light sources. The trigger interface is used so that when a predefined action occurs on the interface, such as flipping a switch or pressing a button, a response action will occur such as turning on a light or power source and then capturing the image that will be processed to determine the cervical dilation.

The display 755, may display the measurement and the visual representation of the cervical region that was processed and generated by the device based on the image sensor data. The display is in electrical communication with the power source, and the processor.

The power source 775, is positioned within the first portion and is in electrical communication with the processor, the camera, the display, and at least one of the structured light sources. The power source may be distributed from the electrical power grid, such as an via an electrical outlet, or for portability, the housing may include an energy storage device(s) such as standard dry cell battery that may be replaced or charged. Other power sources may also be used and are within the spirit and the scope of the present invention.

The structured light source 740, is located in the second portion of the device near the sensor and/or camera. The structured light source is in electrical communication with the power source, the sensor, the processor, and the trigger interface. The structured light source may use white light being easily accessible, or blue light being most accurate and efficient when minimizing effects of reflections and transparency. Colored structured light is also commonly used for measurements in embodiments where the sensor is configured to detect wavelengths of different light spectrums, such as red and/or green projections. Various laser and various patterns of light (dot, grids, crosses, circles, etc.) and wavelengths of light (red, green, blue) can be used accordingly. For example, the structured light source may be a 650 nanometer laser diode. Other laser diodes may be used and are within the spirit and scope of the invention.

The sensor 745, is positioned within the housing, and is configured for capturing image sensor data. The sensor is in electrical communication with the first structured light source such that it is dependent on the pattern being projected onto the cervical region prior to capturing the image data, the power source, and the processor. An imaging sensor is used to obtain a 2D or 3D image from a structured light illumination. If the subject is non planar, the structured light pattern is distorted. As is the case with the cervical region. The light emitted from the laser diode is projected onto the non-planar opening of the cervix. An example of a common imaging sensor used in the medical field is known as Complementary Metal Oxide Semiconductor (CMOS) Imaging Sensors (CIS). These sensors are minimally invasive, they possess high resolutions, low sensitivity, low power consumption, and faster frame rates. Another camera that may be used is one consistent with present technology, such as those used in endoscopes. The cameras may be high-resolution color cameras with photosensitive chips to achieve precise high resolution and color images. Other cameras and sensors may be used and are within the spirit and scope of the invention. The camera 730, is positioned within the second portion, and is configured for capturing and communicating image sensor data to the processor. The camera is in electrical communication with the power source, the processor, and the trigger interface. The camera is a type of imaging sensor, as stated above, a camera may be used to obtain a 2D or 3D image under structured light illumination which may be processed and transmitted to a display for visualization of the dilation of the cervix.

Figure 8:
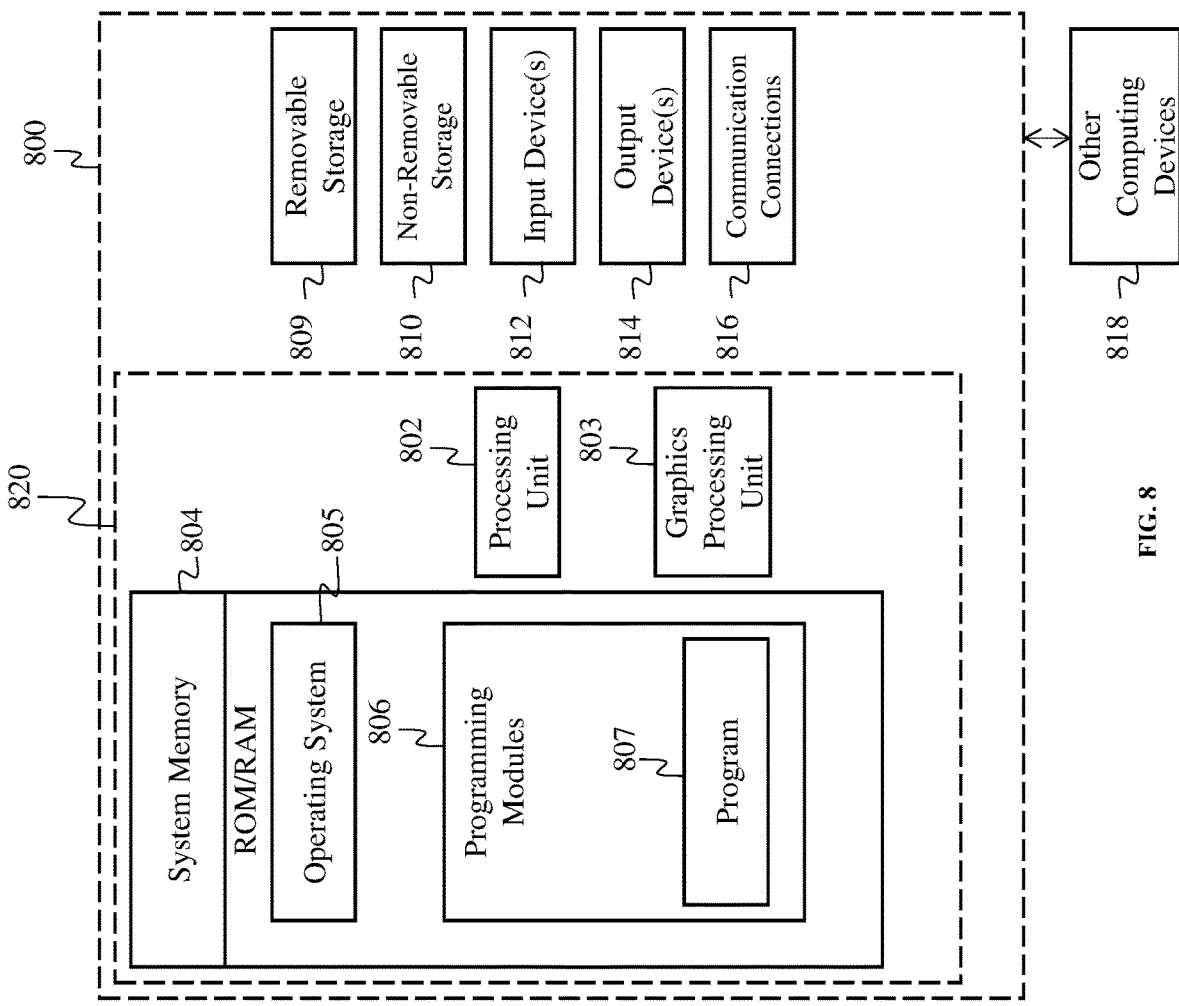
FIG. 8 is an electrical schematic illustrating one embodiment of a processing unit, according to one example of existing technology.

FIG. 8 is a block diagram of the system including an example processor or computing device 800 and other computing devices. Consistent with the embodiments described herein, the aforementioned actions performed by server 802 or computing devices 810, 814, and 818 may be implemented in a computing device, such as the computing device 800 of FIG. 8. Any suitable combination of hardware, software, or firmware may be used to implement the computing device 800. The aforementioned system, device, and processors are examples and other systems, devices, and processors may comprise the aforementioned computing device.

With reference to FIG. 8, a system consistent with an embodiment of the invention may include a plurality of computing devices, such as computing device 800. In a basic configuration, computing device 800 may include at least one processing unit 802 and a system memory 804. Depending on the configuration and type of computing device, system memory 804 may comprise, but is not limited to, volatile (e.g., random access memory (RAM)), nonvolatile (e.g., read-only memory (ROM)), flash memory, or any combination or memory. System memory 804 may include operating system 805, one or more programming modules 806 (such as program module 807). Operating system 805, for example, may be suitable for controlling computing device 800's operation. In one embodiment, programming modules 806 may include, for example, a program module 807. Furthermore, embodiments of the invention may be practiced in conjunction with a graphics library, other operating systems, or any other application program and is not limited to any particular application or system. This basic configuration is illustrated in FIG. 800 by those components within a dashed line 820.

Computing device 800 may have additional features or functionality. For example, computing device 800 may also include additional data storage devices (removable and/or non-removable) such as, for example, magnetic disks, optical disks, or tape. Such additional storage is illustrated in FIG. 8 by a removable storage 809 and a non-removable storage 810. Computer storage media may include volatile and nonvolatile, removable, and non-removable media implemented in any method or technology for storage of information, such as computer readable instructions, data structures, program modules, or other data. System memory

804, removable storage 809, and non-removable storage 810 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information, and which can be accessed by computing device 800. Any such computer storage media may be part of device 800. Computing device 800 may also have input device(s) 812 such as a keyboard, a mouse, a pen, a sound input device, a camera, a touch input device, etc. Output device(s) 814 such as a display, speakers, a printer, etc. may also be included. The aforementioned devices are only examples, and other devices may be added or substituted.

Computing device 800 may also contain a communication connection 816 that may allow device 800 to communicate with other computing devices 818, such as over a network in a distributed computing environment, for example, an intranet or the Internet. Communication connection 816 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both computer storage media and communication media.

As stated above, a number of program modules and data files may be stored in system memory 804, including operating system 805. While executing on processing unit 802, programming modules 806 may perform processes and methods. In other embodiments, the preprogrammed logic may be preprogrammed into the processor or the programming modules. Computing device 800 may also include a graphics processing unit 803, which supplements the processing capabilities of processor 802 and which may execute programming modules 806. The aforementioned processes are examples, and processing units 802, 803 may perform other processes. Other programming modules that may be used in accordance with embodiments of the present invention may include electronic mail and contacts applications, word processing applications, spreadsheet applications, database applications, slide presentation applications, drawing or computer aided application programs, etc.

Generally, consistent with embodiments of the invention, program modules may include routines, programs, components, data structures, and other types of structures that may perform particular tasks or that may implement particular abstract data types. Moreover, embodiments of the invention may be practiced with other computer system configurations, including handheld devices, multiprocessor systems, microprocessor based or programmable consumer electronics, minicomputers, mainframe computers, and the like. Embodiments of the invention may also be practiced in distributed computing environments where tasks are performed by remote processing devices that are linked through a communications network. In a distributed computing environment, program modules may be located in both local and remote memory storage devices.

Furthermore, embodiments of the invention may be practiced in an electrical circuit comprising discrete electronic elements, packaged or integrated electronic chips containing logic gates, a circuit utilizing a microprocessor, or on a single chip (such as a System on Chip) containing electronic elements or microprocessors. Embodiments of the invention may also be practiced using other technologies capable of performing logical operations such as, for example, AND, OR, and NOT, including but not limited to mechanical, optical, fluidic, and quantum technologies. In addition, embodiments of the invention may be practiced within a general-purpose computer or in any other circuits or systems.

Embodiments of the present invention, for example, are described above with reference to block diagrams and/or operational illustrations of methods, systems, and computer program products according to embodiments of the invention. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the invention have been described, other embodiments may exist. Furthermore, although embodiments of the present invention have been described as being associated with data stored in memory and other storage mediums, data can also be stored on or read from other types of computer-readable media, such as secondary storage devices, like hard disks, floppy disks, or a CD-ROM, or other forms of RAM or ROM. Further, the disclosed methods' stages may be modified in any manner, including by reordering stages and/or inserting or deleting stages, without departing from the invention.

Figure 9:
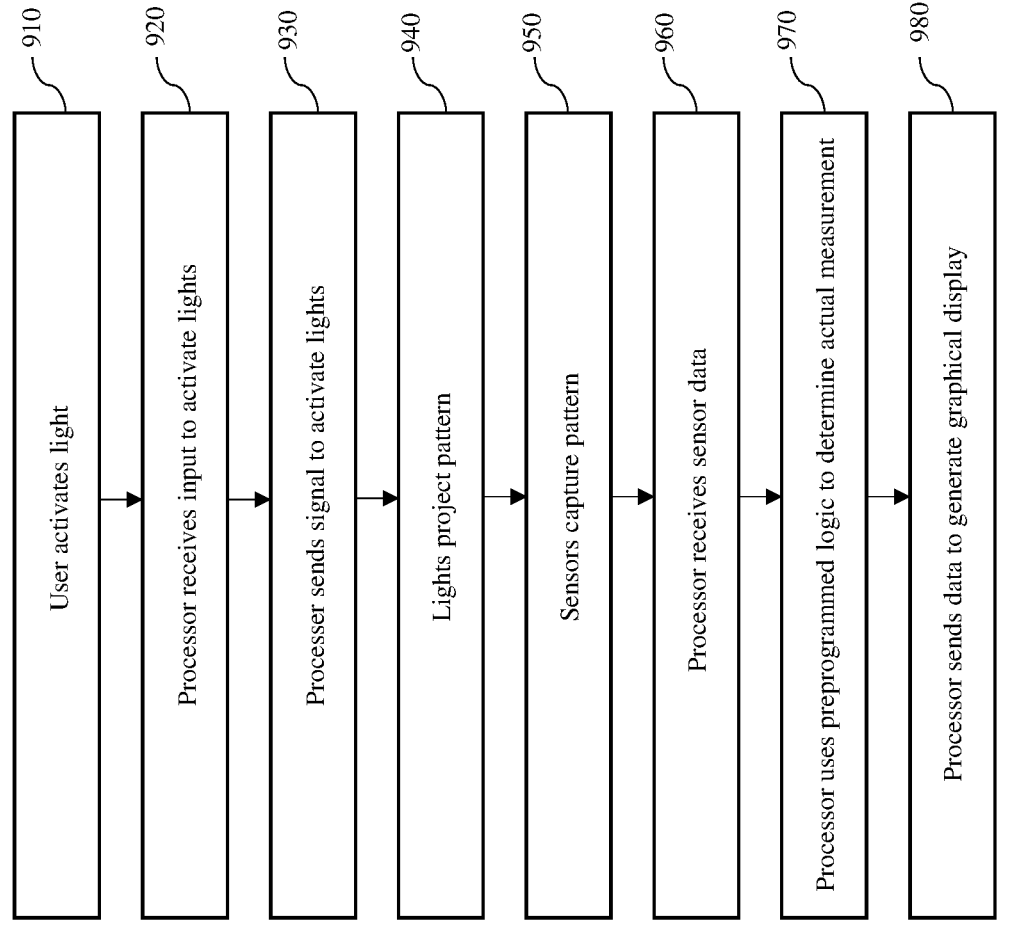
FIG. 9 is a technical method diagram illustrating the order of operations amongst electrical components.

FIG. 9 illustrates the process and steps required starting from when the user turns the structured light on, to the results being presented on the display. To start, in step 910, the user will activate the light. This may be done by pushing a button, flipping a switch, tapping a touch screen surface, stating a word out loud to trigger a voice activated signal, etc. After the button is pushed, a signal is sent through an electrical conductor to the processor with the command to activate light. In step 920, the processor receives the signal and uses its preprogrammed logic to determine the next action based on the signal received. For example, the user interface may cause different signals to the processor, which the processor will use the preprogrammed logic to determine the next appropriate action. In one embodiment, in step 930, the next action or step is to send a signal, through an electric conductor, to the lighting apparatus and to the sensor to turn on the lighting apparatus and to turn on the sensor. When the lighting apparatus and senso receive the signals they turn on or activated.

After the light turns on, as in step 930, next, in step 940, the light projects pattern onto the target area. After the light has projected onto the target area, then in step 950, the sensor then captures the pattern, and sends the data to processor. Next, in step 960, the processor will receive the sensors data, through an electrical conductor. After the processor receives the sensor data, next, in step 970, the processor uses its preprogrammed logic to analyze the data. During this step the processor may use the coordinates of the distortion points to calculate the measurement between. The processor may also use its preprogramed logic to calculate the distance from the end of the probe to the cervix as explained above. Next, in step 980, the processor send date to the display the required graphical display to the user. The display will receive the data and present it to the user in an organized fashion including numerical data, visual drawings being black and white or in color, and possible sounds or alerts. The displays may include the graphical representations illustrated in FIGS. 3, 3E and 3F.

Numerous tests were conducted on the system using the structured light and the processor to measure the dilation of a model cervical region. The results of the test are illustrated in the table below.

| Distance | 3.0 | 5.0 | 7.0 | 4.5 | 6.0 | 7.0 | 5.8 | 6.3 | 7.0 |
|---|---|---|---|---|---|---|---|---|---|
| Target Size | 2.00 | 2.00 | 2.00 | 3.00 | 3.00 | 3.00 | 4.00 | 4.00 | 4.00 |
| Mean | 2.03 | 2.02 | 2.03 | 3.04 | 3.04 | 3.08 | 4.05 | 4.07 | 4.06 |
| Standard Dev | 0.04 | 0.04 | 0.06 | 0.05 | 0.04 | 0.06 | 0.06 | 0.07 | 0.06 |
| Minimum | 1.97 | 1.97 | 1.96 | 2.96 | 2.98 | 2.98 | 3.95 | 3.96 | 3.98 |
| Maximum | 2.12 | 2.09 | 2.11 | 3.10 | 3.11 | 3.15 | 4.16 | 4.20 | 4.17 |

The system was mounted on an optical rail and tested with respect to model opening adjusted for appropriate flesh colors of the cervix and surrounding tissue. The tests were conducted at a distance from 3 cm to 7 cm away from the opening representing the cervical opening. The opening was controlled at a dilation of 2 centimeters, 3 centimeters, and 4 centimeters. The results concluded that the structured light and the processor were able to calculate the dilation within a standard deviation of 0.04 to 0.07 cm. Twenty test samples were collected from each distance and diameter, or 180 sample measurements. Therefore, it is shown that the structured light is highly accurate in measuring the dilation of the cervix as compared to methods and systems of the prior art.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

We claim:

1. A portable system to be inserted within a vaginal channel for measuring dilation of a cervical region within the vaginal channel, the portable system comprising:
    a housing having a first portion and a second portion;
        wherein the first portion is sized to conform to a user's hand thereby defining a handle and the second portion is sized to be inserted into the vaginal channel and capturing the dilation of the cervical region;
    a processor disposed within the housing;
    a structured light source disposed within the second portion;
    a structured projection of light emitted by the structured light source such that it projects onto the cervical region, the structured projection of light comprising a concentrated light element that is at least one of a dot and a line;
    a sensor disposed in the housing, in electrical communication with the structured light source and the processor and configured for capturing image sensor data;
    wherein the processor is configured for:
        receiving the image sensor data from the sensor;
        processing the image sensor data;

detecting a distortion point in the structured projection of light, wherein the distortion point is a distortion in the concentrated light element;

calculating a measurement defining the dilation of the cervical region as a function of a distance between a plurality of distortion points; and transmitting, to a display, graphical display data comprising the dilation.

2. The portable system of claim 1 further comprising:

the display disposed with the first portion; and the processor further configured for generating a visual representation of the cervical region and displaying, on the display, at least one of the measurement of the dilation, and the visual representation of the measurement.

3. The portable system of claim 1 further comprising a trigger interface in electrical communication with the processor, the sensor and at least one of the structured light source, and a second structured light source.

4. The portable system of claim 1 further comprising a power source in electrical communication with the processor, the sensor and the structured light source.

5. The portable system of claim 1 wherein the structured light source projects the structured projection of light onto the cervical region in a first pattern, wherein the first pattern comprises a plurality of concentric rings, wherein each ring of the plurality of concentric rings comprises a plurality of dots.

6. The portable system of claim 1 wherein the second portion is disposed at an angle between 90 degrees and 180 degrees relative to the first portion.

7. The portable system of claim 1 further comprising a second structured light source disposed within the second portion and offset from the structured light source.

8. The portable system of claim 7 further comprising a second structured projection of light emitted by the second structured light source such that it projects onto the cervical region, the second structured projection of light comprising a second concentrated light element that is at least one of a second dot and a second line.

9. The portable system of claim 8 wherein the structured projection of light emitted by the structured light source and the second structured projection of light emitted by the second structured light source form a a unitary pattern of concentrated light such that it is emitted onto the cervical region.

10. The portable system of claim 9, wherein the unitary pattern comprises a plurality of concentric rings, wherein each ring of the plurality of concentric rings comprises a plurality of dots, wherein a first dot forms part of the structured projection of light emitted by the structured light source, and wherein a second dot forms part of the second structured projection of light emitted by the second structured light source.

11. The portable system of claim 10, wherein processing the image sensor data comprises determining at least two distortion points in the unitary pattern when it is projected onto the cervical region.

12. The portable system of claim 11, wherein calculating the measurement comprises determining a distance between the at least two distortion points in the unitary pattern.

13. A portable system to be inserted within a vaginal channel for measuring dilation of a cervical region within the vaginal channel, the portable system comprising:

a housing having a first portion and a second portion;

wherein the first portion is sized to conform to a user's hand thereby defining a handle and the second portion is sized to be inserted into the vaginal channel and capturing the dilation of the cervical region;

a processor disposed within the housing;

a first structured light source disposed within the second portion;

a second structured light source disposed within the second portion;

a first structured projection of light emitted by the first structured light source such that it projects onto the cervical region;

a second structured projection of light emitted by the second structured light source such that it projects onto the cervical region;

wherein each of the first structured projection of light and the second structured projection of light comprise a concentrated light element;

a camera disposed within the second portion;

wherein the camera is configured for capturing and communicating image sensor data to the processor;

a display disposed within the first portion;

wherein the processor is configured for:

receiving the image sensor data from the camera;

processing the image sensor data;

detecting a distortion point in the structured projection of light, wherein the distortion point is a distortion in the concentrated light element;

calculating a measurement comprising the dilation of the cervical region as a function of distance between a plurality of distortion points;

generating a visual representation of the cervical region; and displaying, on the display, at least one of the measurement and the visual representation.

14. The portable system of claim 13 wherein the first structured projection of light emitted by the first structured light source comprises a first pattern of light and the second structured projection of light emitted by the second structured light source comprises a second pattern of light, wherein each of the first pattern of light and the second pattern of light comprise a plurality of dots.

15. The portable system of claim 13 further comprising a trigger interface in electrical communication with the processor, the camera, and at least one of the first structured light source and the second structured light source.

16. The portable system of claim 13 further comprising a power source in electrical communication with the processor, the camera, and at least one of the first structured light source, the second structured light source, and the display.

17. The portable system of claim 13 wherein the first structured light source is offset from the second structured light source.

18. The portable system of claim 13 wherein the first structured projection of light emitted by the first structured light source comprises a first pattern of light and the second structured projection of light emitted by the second structured light source comprises a second pattern of light, wherein the first pattern of light and the second pattern of light are projected onto the cervical region to form a unitary pattern comprising a plurality of concentric rings, wherein each ring of the plurality of concentric rings comprises a plurality of dots.

19. A portable system to be inserted within a vaginal channel for measuring dilation of a cervical region within the vaginal channel, the portable system comprising:

a housing having a first portion and a second portion;

wherein the first portion is sized to conform to a user's hand thereby defining a handle and the second portion is sized to be inserted into the vaginal channel and capturing the dilation of the cervical region;

a processor disposed within the housing;

a first structured light source disposed within the second portion;

a second structured light source disposed within the second portion;

a first structured projection of light emitted by the first structured light source such that it projects onto the cervical region;

a second structured projection of light emitted by the second structured light source such that it projects onto the the cervical region;

wherein each of the first structured projection of light and the second structured projection of light comprise a concentrated light element;

wherein each of the first structured projection of light and the second structured projection of light comprise a plurality of concentrated light elements arranged in a pattern of light that is projected onto the cervical region;

a camera disposed within the second portion;

wherein the camera is configured for capturing and communicating image sensor data to the processor;

a display disposed within the first portion;

wherein the processor is configured for:

receiving the image sensor data from the camera;

processing the image sensor data, wherein processing comprises determining at least two distortion points in the pattern of light when it is projected onto the cervical region;

calculating a measurement defining the dilation of the cervical region, wherein calculating the measurement comprises determining a distance between the at least two distortion points in the pattern of light; wherein a distortion point is a distortion in a concentrated light element of the plurality of concentrated light elements arranged in the pattern of light;

generating a visual representation of the cervical region; and displaying, on the display, the measurement and the visual representation of the cervical region;

a trigger interface disposed in the first portion in electrical communication with the processor, the camera, and at least one of the first structured light source, and the second structured light source; and a power source disposed in the first portion and in electrical communication with the processor, the camera, and at least one of the first structured light source, the second structured light source, and the display.

* * * * *